United States Patent [19]

Crosby

[11] Patent Number: 4,613,498

[45] Date of Patent: Sep. 23, 1986

[54] HEMORRHOID MEDICATION

[76] Inventor: Frank Crosby, 1745 Texar Dr., Pensacola, Fla. 32503

[21] Appl. No.: 664,313

[22] Filed: Oct. 24, 1984

[51] Int. Cl.$^4$ ............................................. A61K 33/06
[52] U.S. Cl. ..................................... 424/154; 514/882
[58] Field of Search ................ 424/154; 514/305, 161, 514/882

[56] References Cited

U.S. PATENT DOCUMENTS 120,879  11/1871  Irwin .

OTHER PUBLICATIONS

*Handbook of Nonprescription Drugs,* Fifth Edition, 1977 p. 68, published by Amer. Pharm. Assoc., Wash. D.C.

*Primary Examiner*—Frederick E. Waddell
*Attorney, Agent, or Firm*—George A. Bode

[57]  ABSTRACT

An anorectal medication for the treatment of hemorrhoids utilizing a mixture of ingredients in an ointment base. A powdered mixture of alum, quinine sulfate and aspirin is mixed with petroleum jelly to form an ointment which is applied topically to the affected area.

4 Claims, No Drawings

HEMORRHOID MEDICATION

BACKGROUND OF THE INVENTION

1. Field of the Invention

The invention relates to a medication for the treatment of anorectal disease or irritations and in particular relates to a medication for the treatment of hemorrhoids.

2. General Background

The most common of the diseases treated by the medication disclosed herein is hemorrhoids or piles. The major problems which exist in healing of such diseases are well known. Tissues which are already swollen and inflamed are subjected to stretching, tearing, and irritation which greatly impedes the natural healing process. Compositions in the prior art treatments have been developed which generally relieve either the itching or inflammation with varying success. The efficacy of these prior art treatments in relieving or curing the symptoms of such diseases is uncertain. Prior art patents of which applicant is aware include the following:

U.S. Pat. No. 4,192,866, issued to Anderson, entitled "Anorectal Medication", discloses a preparation for the treatment of anorectal diseases, especially hemorrhoids, comprising polyglycerides and ripe berry products of the plant "Solanum carolinese" (Horse Nettle). The polyglycerides are heated and the fragmented berries are then added thereto. Sublimed sulfur, ammonium alum, and turpentine are added to the mixture which is agitated and filtered, thereby producing a substantially homogeneous medication. The berries are the active healing agent and provided in a medium which is normally animal fat or a vegetable oil.

U.S. Pat. No. 4,265,883, issued to M. R. Cameron, entitled "Composition And Process For Treating Uterine Prolapse", discloses a process of treating a female having uterine prolapse which comprises topically applying an ointment to the uterus comprising alum, glycerine, and a soft solid such as hydrogenated vegetable oil, petroleum jelly or lard. It also preferably comprises epsom salt and a local anesthetic such as tetracaine hydrochloride. The composition is also disclosed as being useful for treating sores, boils, and hemorrhoids and may be applied directly or as a gauze sheet having the mixture applied thereto.

SUMMARY OF THE PRESENT INVENTION

The present invention is an anorectal medication utilizing a mixture of ingredients in a semisolid or ointment base carrying agent. A semisolid carrying agent such as petroleum jelly is mixed with alum, quinine, and aspirin. The preparation is normally applied as an ointment directly to the affected area. The preparation helps to lubricate and add flexibility to the tissues, reduce swelling, inflammation, and pain and promote healing.

In view of the above, it is an object of the present invention to provide a preparation for use in the treatment of anorectal disease and irritation.

It is another object of the present invention to provide a preparation which reduces swelling, inflammation, and pain and promotes healing.

DETAILED DESCRIPTION OF THE PREFERRED EMBODIMENT

In general, the preparation of the present invention utilizes active ingredients comprising alum, quinine, and aspirin. The carrying agent used for the active ingredients is preferably a semisolid at room and body temperature to provide for ease of application. The carrying agent could also be used in the form of a suppository which melts at body temperature, but the ointment form is preferred due to ease of application.

Petrolatum, commonly known as petroleum jelly, is a purified mixture of semisolid hydrocarbons obtained from petroleum and commonly used as an ointment base. In addition to being a suitable carrying agent for the active ingredients of the preparation of the invention, it also serves as a protective dressing and soothing emollient application to the skin. It provides lubrication, adds flexibility to the affected tissue, and serves as a protective layer against foreign material.

Another suitable base or carrying agent is a medicated petroleum jelly, such as that marketed under the trade name "Carbolated Vaseline." This provides an additional medication, chloroxylenol, an antiseptic which also helps to promote healing.

The alum, which is either aluminum potassium sulfate or aluminum ammonium sulfate or a mixture of the two, serves as the preferred astringent although other astringents may be used. The astringent action causes shrinkage or contraction of the tissues to aid in stopping bleeding from any exposed blood capillaries in the area of the affected tissue. The alum does not directly cause vascular constriction and still allows blood flow to the damaged tissue being healed. The alum is added to the ointment base in a preferred ratio of one level teaspoon or approximately 3 to 4 grams of alum per ounce of ointment base.

The quinine is used in the powder form of one of its salts, preferably quinine sulfate. The quinine sulfate salt exhibits analgesic, antipyretic, and sclerosing properties. All of the properties are beneficial in the preparation for the relief of pain, reduction of fever and promotion of healing of damaged tissue by hardening due to an increase in connective tissue. The quinine sulfate powder is thoroughly mixed with the alum and ointment base in a preferred ratio of 100 milligrams of quinine sulfate per ounce of ointment base.

Aspirin, or acetylsalicylic acid, is well known for it analgesic, antipyretic, and antiinflammatory properties, and thus complements the effects of the quinine by the addition of antiinflammatory action. The aspirin is added to the ointment base in a preferred ratio of 10 grains (650 milligrams) of aspirin per ounce of ointment base. Two tablets or capsules of aspirin commercially available, such as that marketed under the trade name ANACIN, may also be used. This would provide approximately 800 milligrams of aspirin per ounce of ointment base.

In preparing the medication the alum, quinine, and aspirin are provided or ground into a fine powder to be mixed together. After the powders of these ingredients are thoroughly mixed, the mixture is then incorporated into the petroleum jelly. The grinding of each ingredient into a fine powder and mixing of ingredients before incorporation into the petroleum jelly helps to ensure even dispersion of the active ingredients in the carrying agent.

Although the quantity of ingredients may be varied, the preferred embodiment of the preparation constitutes 1 ounce petroleum jelly, 1 teaspoon (3-4 grams) of alum, 100 milligrams quinine sulfate, and 650 milligrams acetylsalicylic acid.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A composition for the topical treatment of hemorrhoids, comprising:
   a. a semi-solid carrying agent comprising one (1) ounce of petroleum jelly;
   b. three (3) to four (4) grams of powdered alum mixed with said carrying agent;
   c. one hundred (100) milligrams quinine sulfate powder mixed with said carrying agent; and
   d. six hundred and fifty (650) to eight hundred (800) milligrams powdered acetylsalicylic acid mixed with said carrying agent.
2. The composition of claim 1, wherein said petroleum jelly contains chloroxylenol.
3. A composition for the topical treatment of hemorrhoids, comprising:
   a. approximately 1 ounce of a semisolid carrying agent comprising petroleum jelly;
   b. approximately 3-4 grams powdered alum mixed with said carrying agent;
   c. approximately 100 milligrams quinine sulfate powder mixed with said carrying agent; and
   d. approximately 650 milligrams of powdered acetylsalicylic acid mixed with said carrying agent.
4. The composition of claim 3, wherein said petroleum jelly contains chloroxylenol.

* * * * *